United States Patent [19]
Razzano

[11] Patent Number: 5,989,575
[45] Date of Patent: Nov. 23, 1999

[54] FINGERNAIL LACQUER COMPOSITION

[76] Inventor: Dominick D. Razzano, 5902 NW. 40th Ter., Virginia Gardens, Fla. 33166

[21] Appl. No.: 09/063,156

[22] Filed: Apr. 20, 1998

Related U.S. Application Data

[63] Continuation-in-part of application No. 09/021,652, Feb. 10, 1998.
[51] Int. Cl.⁶ .............................. A61K 6/00; A61K 7/00; A61K 7/04
[52] U.S. Cl. ............................................. 424/401; 424/61
[58] Field of Search ........................ 424/61, 401

[56] References Cited

U.S. PATENT DOCUMENTS 4,166,054  8/1979  Meeske et al. ............................ 260/23

*Primary Examiner*—Thurman K. Page
*Assistant Examiner*—Sharon Howard
*Attorney, Agent, or Firm*—Robert M. Downey, P.A.

[57] ABSTRACT

A composition for application to fingernails and toe nails includes a binder and a pigment, the binder including volatile and non-volatile components and the pigment being present in the composition in an amount of between 30% to 83% of the total volume of the non-volatile portion of the composition, creating a physical action upon drying of a layer of the composition applied to the nails, wherein a lack of cohesive strength between the pigment and binder results in formation of random cracks in the applied layer.

8 Claims, 1 Drawing Sheet

U.S. Patent Nov. 23, 1999 5,989,575

FINGERNAIL LACQUER COMPOSITION

This application is a continuation-in-part application of co-pending patent application Ser. No. 09/021,652 filed on Feb. 10, 1998.

BACKGROUND OF THE INVENTION

1. Field of the Invention

The present invention relates to a cosmetic preparation and method for applying the preparation to fingernails and toe nails.

2. Description of the Related Art

The art is crowded with various nail polish compositions and methods of applying nail art designs to fingernails. Such methods and compositions are no longer limited to a single, uniform color of nail polish applied to all of one's fingernails or toe nails. It is now commonplace to paint multi-color designs on each nail, sometimes adding sparkles, decals, and other design elements to enhance the overall appearance of the polished nails. This is usually done by airbrushing or free hand painting, both of which require a considerable degree of skill and artistic ability. For this reason, anything beyond conventional polishing of nails with a uniform color must usually be done by a professional at a nail salon.

Now that nail art has gone beyond the traditional single color and french manicure, new and more unusual appearances are becoming increasingly popular. In spite of the more contemporary, and sometimes wild painted nail designs and colors which have set a trend in the cosmetic industry, the present invention provides a highly unique crackle appearance which has never been achieved in the nail polish art prior to this invention. The crackle appearance which results using the composition of the present invention is similar to an appearance known in the furniture industry for creating an antique finish. However, the crackle lacquer used in the furniture industry is not suitable for use in the cosmetic industry, as it contains a number of toxic components which present a health hazard. For this reason, crackle lacquers presently known in the art are not approved by the Food and Drug Administration for use as a cosmetic product. And, while others may have attempted to achieve the crackle effect in a nail polish composition, it is believed that such attempts have been unsuccessful due to the difficulty in producing a non-toxic crackle composition which has physical characteristics that make it suitable for application by both brushing and spraying on fingernails and toe nails.

Accordingly, there is a need in the cosmetic industry for a non-toxic lacquer composition for application to fingernails and toe nails, either by brushing or spraying, and wherein the lacquer composition is physically structured to provide a crackle appearance upon drying. In fulfilling this need, the present invention provides for a non-toxic cosmetic preparation and method of applying the preparation to fingernails and toe nails, wherein the cosmetic preparation is structured to undergo a physical change upon drying to produce the desired crackle appearance.

SUMMARY OF THE INVENTION

The present invention is directed to a cosmetic preparation and a method of applying the cosmetic preparation to fingernails and toe nails. The cosmetic preparation includes a crackle composition for application to nails which have one or more coats of previously applied conventional colored nail polish thereon. This crackle composition includes a pigment and a binder provided in a ratio to create a physical action upon drying of a layer applied to the nails, wherein a lack of cohesive strength between the pigment and the binder results in shrinking of the applied layer to form cracks therein. The previously applied underlying colored nail polish is thus visible through the cracks formed in the overlying layer of the crackle composition which is of a different color.

Depending upon the surface quality and chemical composition of the conventional fingernail polish which has been applied before application of the cosmetic preparation of the present invention, it may be necessary to apply a clear coat barrier composition in covering relation to the fingernail polish prior to application of the crackle coat composition. This colorless, transparent base composition can be either brushed or sprayed on the fingernails to provide a layer covering the surface of the fingernail polish. After allowing the base coat to dry for three to ten minutes at ambient temperature, the crackle coat composition is applied. The crackle coat composition can be either brushed or sprayed on the nails to provide a uniform layer thereon. During air drying, which requires approximately five to ten minutes, cracking of the applied crackle coat occurs and two colors become visible; the color of the crackle coat and the color of the conventional fingernail polish which appears through the cracks of the crackle coat layer.

To obtain a high gloss over the crackle coat, a conventional clear gloss layer can be brushed or sprayed over the crackle coat layer after the crackle coat layer has completely dried. For the highest gloss, two coats of clear gloss lacquer can be applied.

BRIEF DESCRIPTION OF THE DRAWINGS

For a fuller understanding of the nature of the present invention, reference should be made to the following detailed description taken in connection with the accompanying drawings in which.

DETAILED DESCRIPTION OF THE PREFERRED EMBODIMENT

Figure 1:
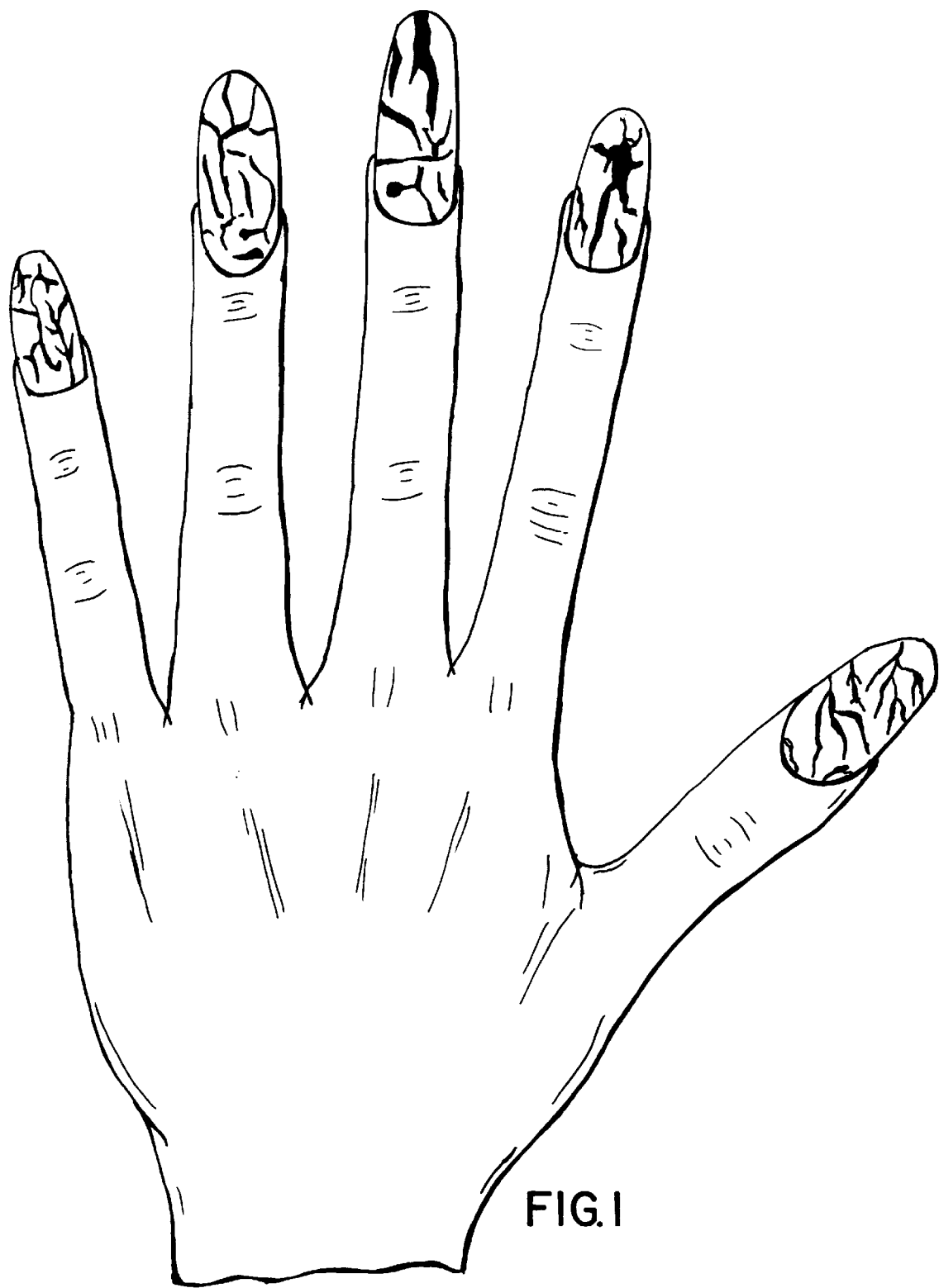
FIG. 1 is a top plan view of a hand having fingernails treated with the cosmetic preparation of the present invention, wherein each of the nails is shown with a different crackle coat pigment and nail polish color combination to illustrate various appearances achieved using the cosmetic preparation of the present invention.

The cosmetic preparation of the present invention provides a novel and distinct visual appearance on polished fingernails. In contrast to the one solid color appearance produced by conventional fingernail polish products, the cosmetic preparation of the present invention produces two colors with a randomly created crackle design. More specifically, the top crackle coat appears as one color while a different color of the underlying coat of conventional nail polish is visible through the cracks formed in the top crackle coat, as seen on the fingernails in FIG. 1.

The cosmetic preparation of the present invention is useful in combination with virtually any commercially available fingernail polish. The cosmetic preparation includes two separate compositions which are applied independently of the other by either brushing or spraying. Specifically, the cosmetic preparation includes a clear coat base composition which is applied to the surface of dry colored fingernail polish which has been previously painted on the fingernails or toe nails. The clear coat base composition is applied in a uniform layer by either brushing or spraying over the surface of the polished nails, and allowed to dry for three to ten minutes at ambient temperature.

The cosmetic preparation further includes a crackle coat composition which comprises non-toxic ingredients, including a binder portion and a pigment portion. The binder portion includes volatile and non-volatile components, and more specifically, select resins and solvents. The pigment portion includes one or more color pigments and a pigment extender. As a practical matter, the pigments used in nail polish must conform to appropriate national legislation. The color pigments used in the composition of the present invention are all certified by the Food & Drug Administration (FDA). In particular, the liquid or vehicle portion of the crackle coat composition is free from toluol, methyl ethyl ketone, xylol, and formaldehyde. The crackle coat composition is applied to the exposed, dry surface of the base coat by either brushing or spraying. The applied layer of the crackle coat should be uniform across the entire upper side of the nails. During drying for a period of five to ten minutes at ambient temperature, the applied layer of crackle coat forms random cracks in the applied layer, thereby exposing the color of the underlying conventional nail polish. This phenomenon of cracking of the crackle coat layer is a physical reaction which results from over pigmentation. More specifically, the crackle coat composition includes a pigment and a binder which are provided in a ratio that creates a lack of cohesive strength between the pigment and binder. This results in shrinking of the applied layer of the crackle coat composition when drying, thereby creating the desired cracks. The amount of pigment in the composition, or pigment volume concentration (pvc), is expressed in terms of the percentage of the volume of pigment in relation to the total volume of the non-volatile portion of the composition. Satisfactory results have been achieved with a pigment volume concentration ranging between 30% and 83%. However, the best results, to date, have been achieved with a pigment volume concentration ranging between 63% and 83%.

In many instances, the clear coat base composition can be omitted, depending upon the surface quality and chemical composition of the particular fingernail polish which has been previously applied to the nails. However, to ensure a uniform foundation for subsequent coatings, application of the clear coat base composition is generally recommended prior to applying the crackle coat composition. The clear base coat further prevents bleeding or migration of the conventional nail polish through to the subsequently applied crackle coat composition, thereby serving as a barrier.

The compositions of the present invention include various solvents, resins, FDA certified pigments, and pigment extenders. The following are examples of each of these components.

Solvents n-butyl acetate (ester solvent)

Ethyl acetate (ester solvent)

Propylene glycol methyl ether acetate (ester solvent)

Isopropyl alcohol (oxygenated solvent)

Dipropylene glycol methyl ether (glycol ether solvent)

V.M.P. naphtha/petroleum naphtha (aliphatic petroleum solvent)

Mineral spirits (aliphatic petroleum solvent)

Resins

Acrylic resin (a polymer of acrylic-methacrylic acids and their esters)

Maleated-rosin (rosin-maleic adduct)

Nitrocellulose (soluble cellulose ester)

Pigment

FD&C colors (FDA certified pigments)

Pigment Extenders

Magnesium silicate (Vantac 6H)

Silicone dioxide (Amorphous silica)

Aluminum stearate

Calcium carbonate

Barium sulfate

Aluminum silicate

Calcium silicate

Calcium sulfate

The following examples are illustrative of compositions of the cosmetic preparation of the present invention.

EXAMPLE 1

A clear coat base composition, comprising petroleum naphtha, n-butyl acetate, ¼ sec nitrocellulose, a plasticizer, propylene glycol methyl ether acetate, and ethyl acetate was prepared with the following ingredients in the indicated concentrations:

| Ingredient | Weight | Volume | Supplier |
|---|---|---|---|
| Petroleum naphtha (VMP) | 105.720 lbs. | 17.388 gal. | Shell Chemical Co. Houston, TX |
| n-butyl acetate | 135.770 lbs. | 18.598 gal. | Eastman Chemical Kingsport, TN |
| ¼ sec nitro-cellulose (70%) | 93.000 lbs. | 8.942 gal. | Hercules Wilmington, DE |
| Isopropyl alcohol | 21.500 lbs. | 3.307 gal. | Eastman Chemical Kingsport, TN |
| 2-ethylhexyl diphenyl phosphate (Santicizer 141) | 9.500 lbs. | 1.044 gal. | Monsanto Springfield, MA |
| #15 Castor Oil | 3.000 lbs. | 0.350 gal. | Cas Chemical Bayonne, NJ |
| Propylene glycol methyl ether acetate (P.M.A.) | 25.800 lbs. | 3.108 gal. | Dow Chemical Midland, MI |
| Ethyl acetate | 18.770 lbs. | 2.536 gal. | Eastman Chemical Kingsport, TN |
| TOTAL | 413.060 lbs. | 55.273 gal. (1 drum) | |

Description: A one drum batch (413 pounds) of the clear coat base composition was prepared in accordance with the following procedure. The ingredients, as listed above, are added, one at a time, in the order presented, beginning with petroleum naphtha. After adding each ingredient, the mixture is stirred until the added ingredient is completely blended with the previously added ingredients. This process of adding and stirring in each ingredient is continued until all ingredients have been completely blended in a homogenous mixture. The resultant mixture is then thinned using butyl acetate and a brushing viscosity of 35 secs. No. 2 Zahn Cup is achieved.

EXAMPLE 2

A crackle coat composition, in accordance with a preferred embodiment of the present invention, comprises a first mixture and a second mixture. The pigment portion in the crackle composition includes one or more FDA certified pigments and a pigment extender. The pigment portion is present in a preferred pigment volume concentration (pvc) to produce shrinking and cracking of an applied layer of the composition during the drying process. In one example, the crackle coat composition was prepared with the following ingredients in the indicated concentrations:

| Ingredient | Weight | Volume | Supplier |
|---|---|---|---|
| The First Mixture | | | |
| n-butyl acetate | 116.00 lbs. | 15.89 gal. | Eastman Chemical Kingsport, TN |
| 5 sec ss/nc (spirit soluble/ nitrocellulose) | 9.20 lbs. | 0.88 gal. | Hercules Wilmington, DE |
| Isopropyl alcohol | 44.80 lbs. | 6.89 gal. | Eastman Chemical Kingsport, TN |
| Magnesium silicate (Vantac 6H) | 76.60 lbs. | 3.36 gal. | |
| Petroleum Naphtha (V.M.P.) | 64.20 lbs. | 10.56 gal. | Shell Chemical Co. Houston, TX |
| | 310.80 lbs. | 37.58 gal. | |
| The Second Mixture | | | |
| n-butyl acetate | 36.34 lbs. | 4.98 gal. | Eastman Chemical Kingsport, TN |
| Acrylic resin (Paraloid B72) | 3.12 lbs. | 0.33 gal. | ROH M & Haas Midland, MI |
| Maleated-rosin (Beckacite 111) | 8.94 lbs. | 0.91 gal. | Arizona Chemical Panama City, FL |
| FDA certified color (pigment) | 28.50 lbs. | 1.80 gal. | Hilton-Davis Newark, NJ |
| | 76.90 lbs. | 8.02 gal. | |
| Total Composition: | 387.70 lbs. | 45.6 gal. | |

Description: A 45.6 gallon batch of the crackle coat composition, according to the above example, is prepared in accordance with the following procedure. The ingredients of each mixture, as listed above, are added, one at a time, in the order presented. For example, with the first mixture, n-butyl acetate is mixed with 5 sec ss/nc and stirred until the ingredients are completely blended. Thereafter, the subsequently listed ingredients are mixed, one at a time, until all of the ingredients have been completely blended to form a homogenous mixture. The second mixture is then added slowly to the first mixture, with agitation, and blended until the first and second mixtures are completely blended in a homogenous composition.

The final crackle coat composition is thinned, using n-butyl acetate, to achieve the desired viscosity. In the above example, the composition was thinned to a viscosity of 22–25 secs. No. 2 Zahn Cup or 50–60 poises.

EXAMPLE 3

To prevent some settling, an anti-settling component can be added to the crackle coat composition. An example of the crackle coat composition containing the anti-settling component is set forth below:

| Ingredient | Weight | Volume | Supplier |
|---|---|---|---|
| The First Mixture | | | |
| n-butyl acetate | 116.00 lbs. | 15.89 gal. | Eastman Chemical Kingsport, TN |
| 5 sec ss/nc (spirit soluble/ nitrocellulose) | 9.20 lbs. | 0.88 gal. | Hercules Wilmington, DE |
| Isopropyl alcohol | 44.80 lbs. | 6.89 gal. | Eastman Chemical Kingsport, TN |
| Magnesium silicate (Vantac 6H) | 76.60 lbs. | 3.36 gal. | |
| Petroleum Naphtha (V.M.P.) | 64.20 lbs. | 10.56 gal. | Shell Chemical Co. Houston, TX |
| | 310.80 lbs. | 37.58 gal. | |
| Anti-Settling Mixture | | | |
| Tri alkyl ammonium hectiorite (Bentone 27) | 4.00 lbs. | 0.26 gal. | Rheox Inc. Hightstown, NJ |
| Ethyl acetate | 33.60 lbs. | 4.48 gal. | Eastman Chemical Kingsport, TN |
| Isopropyl alcohol | 2.40 lbs. | 0.36 gal. | Eastman Chemical Kingsport, TN |
| | 40.00 lbs. | 5.10 gal. | |
| The Second Mixture | | | |
| n-butyl acetate | 36.34 lbs. | 4.98 gal. | Eastman Chemical Kingsport, TN |
| Acrylic resin (Paraloid B72) | 3.12 lbs. | 0.33 gal. | ROH M & Haas Midland, MI |
| Maleated-rosin (Beckacite 111) | 8.94 lbs. | 0.91 gal. | Arizona Chemical Panama City, FL |
| FDA certified color (pigment) | 28.50 lbs. | 1.80 gal. | Hilton-Davis Newark, NJ |
| | 76.90 lbs. | 8.02 gal. | |
| Total Composition: | 427.70 lbs. | 50.7 gal. | |

Description: A 50.7 gallon batch of the crackle coat composition was prepared, as set forth in the above example, incorporating the anti-settling component. The ingredients in the first mixture portion and the second mixture portion were mixed, as described in connection with the description of Example 2. However, prior to combining the first mixture with the second mixture, the anti-settling component is added to the first mixture. The ingredients of the anti-settling component are first combined under strong agitation. Upon cooling of the anti-settling component, the mixture takes on a slight gel-like structure. At this point, the anti-settling component is added to the first mixture, stirring until completely blended to form a homogeneous mixture. Thereafter, the first mixture, containing the anti-settling component, is added to the second mixture in the manner described in connection with Example 2.

The final composition is thinned using n-butyl acetate to achieve the desired viscosity. In the above example, a preferred viscosity is between 22–25 secs. No. 2 Zahn Cup or 50–60 poises.

The composition of Example 3 yields 8.52 lbs. per gallon. The percentage of non-volatile ingredients in the composition (Example 3) is 32.2%. The pigment volume concentration is 75.3%.

It is recognized that the amount of pigment ingredient utilized may vary. However, one skilled in the art will recognize that the amount of pigment incorporated into the composition will depend upon the specific properties of the pigment or pigments utilized, e.g., density and oil adsorption, as well as the viscosity of the composition and the need to adjust the pigment percentage to achieve the optimum results of crackle characteristics.

Furthermore, the specific mixing equipment used during the manufacturing of the composition may vary and it is recognized by those skilled in the art that the specific order and amount of each of the ingredients may change depending upon the particular mixing equipment used. To this end, the composition may have to be fine tuned to accommodate the specific manufacturing equipment, as well as the commercial production standards.

While the instant invention has been described in accordance with preferred embodiments thereof, it is recognized that departures from the instant disclosure may be made within the spirit and scope of the present invention, and such departures shall not be limited except as set forth in the following claims as interpreted under the doctrine of equivalents.

What is claimed is:

1. A lacquer composition for application to fingernails and toe nails comprising:

a non-toxic binder portion comprising volatile and non-volatile components;

a non-toxic pigment portion; and said pigment portion being present in the composition in a volume of concentration ranging between 30% and 83% of the total volume of a non-volatile portion of the composition and said volume of concentration of said pigment portion causing the formation of random cracks in said composition upon drying of an applied layer of said composition.

2. A lacquer composition as recited in claim 1 wherein said binder portion includes:

an acrylic resin;

a maleated-rosin; and solvents.

3. A lacquer composition as recited in claim 2 wherein said pigment portion includes:

at least one FDA certified color; and a pigment extender.

4. A lacquer composition as recited in claim 1 wherein said non-volatile components of said binder include resins selected from the group consisting of:

acrylic resin;

maleated-rosin; and nitrocellulose.

5. The lacquer composition as recited in claim 1 wherein said volatile components of said binder portion include solvents selected from a group consisting of:

n-butyl acetate;

ethyl acetate;

propylene glycol methyl ether acetate;

isopropyl alcohol;

dipropylene glycol methyl ether;

petroleum naphtha; and petroleum solvent.

6. A lacquer composition as recited in claim 1 wherein said pigment portion includes at least one pigment extender selected from the group consisting of:

magnesium silicate;

silicon dioxide;

aluminum stearate;

calcium carbonate;

barium sulfate;

aluminum silicate;

calcium silicate; and calcium sulfate.

7. A method of decorating fingernails and toe nails comprising the steps of:

providing a lacquer composition comprising:
  a non-toxic binder portion comprising volatile and non-volatile components;
  a non-toxic pigment portion;
  said pigment portion being present in the lacquer composition in a volume of concentration ranging between 30% and 83% of the total volume of a non-volatile portion of the lacquer composition;

applying a layer of said lacquer composition to a surface on a nail;

drying said applied layer; and forming random cracks in said applied layer to visibly expose said surface through said randomly formed cracks.

8. A method of decorating fingernails and toe nails comprising the steps of:

providing a lacquer composition comprising:
  a non-toxic binder portion comprising volatile and non-volatile components;
  a non-toxic pigment portion;

applying a layer of said lacquer composition to a surface on a nail;

drying said applied layer; and causing random cracks to form in said applied layer by providing said pigment portion in a volume of concentration ranging between 30% and 83% of the total volume of a non-volatile portion of the composition, thereby visibly exposing said surface through said cracks in said applied layer.

* * * * *